| United States Patent [19] | [11] | 4,358,593 |
|---|---|---|
| Jones et al. | [45] | Nov. 9, 1982 |

[54] PROCESS FOR PREPARING 3-(4-AMINOETHOXYBENZOYL)BENZO[B]-THIOPHENES

[75] Inventors: Charles D. Jones, Indianapolis, Ind.; Mary E. Goettel, Chesterland, Ohio

[73] Assignee: Eli Lilly and Company, Indianapolis, Ind.

[21] Appl. No.: 246,334

[22] Filed: Apr. 3, 1981

[51] Int. Cl.$^3$ .................... C07D 333/58; C07D 409/12
[52] U.S. Cl. .................... 546/202; 260/330.3; 544/146; 549/51; 548/525
[58] Field of Search .................... 549/51; 260/326.35, 260/326.5 SA, 330.3; 544/146; 546/202

[56] References Cited

U.S. PATENT DOCUMENTS 3,947,470  3/1976  Brenner et al. .................... 260/330.5
3,983,245  9/1976  Ladd and Ross .................... 424/285
4,001,426  1/1977  Brenner et al. .................... 424/285
4,133,814  1/1979  Jones et al. .................... 260/326.5 SA

OTHER PUBLICATIONS

McOmie, Ed., Protective Groups In Organic Chemistry, Plenum Press, London, 1973, Chapters 3 and 4.
Morrison et al., Organic Chemistry, Allyn And Bacon, Inc., Boston 1970, pp. 731–733.
Looker and Thatcher, *J. Org. Chem.* 19, 784–788 (1954).

*Primary Examiner*—Richard Raymond
*Attorney, Agent, or Firm*—Joseph A. Jones; Arthur R. Whale

[57] ABSTRACT

The use of particularly advantageous protecting groups for the hydroxy groups of 6-hydroxy-2-(4-hydroxyphenyl)benzo[b]thiophenes provides a high-yielding process for the preparation of such compounds having a 4-(2-aminoethoxy)benzoyl 3-group.

19 Claims, No Drawings

PROCESS FOR PREPARING 3-(4-AMINOETHOXYBENZOYL)BENZO[B]THIOPHENES

BACKGROUND OF THE INVENTION

1. Field of the Invention

This invention belongs to the field of pharmaceutical chemistry, and provides an advantageous process for preparing a group of 6-hydroxy-2-(4-hydroxyphenyl)-3-[4-(2-aminoethoxy)benzoyl]benzo[b]thiophenes. The process makes use of certain particularly advantageous protecting groups for the hydroxy groups, and provides the desired compounds in excellent yield.

2. State of the Art

Most of the compounds which are prepared by the process of this invention were taught in U.S. Pat. No. 4,133,814, of Jones and Suarez, which patent shows a number of processes for preparing them. The patent shows the use of phenacyl, halophenacyl, and alkyl protecting groups. The process of this invention has been found to be much more advantageous than those shown by the patent.

Many types of protecting groups have been proposed and used for hydroxy groups. The standard textbook, Protective Groups in Organic Chemistry, Plenum Press, New York, 1973, J. F. W. McOmie, Ed., devotes chapters 3 and 4 to the subject. Many types of protecting groups are proposed, including alkyl groups, benzoyl groups, triarylmethyl groups, trimethylsilyl groups, acetals, ketals, esters of many types, substituted esters such as haloacetates and phenoxyacetates, carbonates, sulfonates, benzylidineacetals, benzoates and substituted benzoates.

SUMMARY OF THE INVENTION

This invention provides a process for preparing a compound of the formula

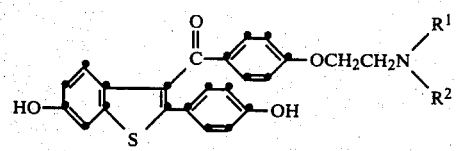

wherein $R^1$ and $R^2$ are independently $C_1$–$C_4$ alkyl, or combine to form $C_4$–$C_6$ polymethylene of —$(CH_2)_2O(CH_2)_2$—; which process comprises acylating a compound of the formula

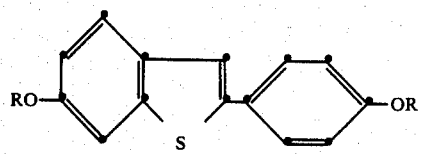

wherein R is —$COR^3$ or —$SO_2R^3$, and $R^3$ is $C_1$–$C_4$ primary or secondary alkyl, trifluoromethyl, trichloromethyl, phenyl, p-tolyl, p-anisyl, or mono- or di(halo or nitro)phenyl;

under Friedel-Crafts conditions with an acylating agent of the formula

wherein $R^5$ is X or

X is chloro, bromo or —$SO_2R^3$;
and $R^4$ is chloro, bromo, iodo, or an activating ester group;
when $R^5$ is X, displacing the X group with an amine of the formula $$HN\begin{matrix}R^1\\R^2\end{matrix};$$

and cleaving the R groups.

DESCRIPTION OF THE PREFERRED EMBODIMENTS

In this document, all temperatures will be stated in degrees Celsius. All amounts, ratios, concentrations, proportions and the like will be stated in weight units, unless otherwise stated, except for ratios of solvents, which are in volume units.

In the general formula above, the general terms bear their usual meanings. For example, the term $C_1$–$C_4$ primary or secondary alkyl refers to groups such as methyl, ethyl, propyl, s-butyl, i-butyl and the like. The term $C_1$–$C_4$ alkyl includes the above groups and also includes t-butyl. The term $C_4$–$C_6$ polymethylene refers to tetramethylene, pentamethylene and hexamethylene.

The following group of representative products of the process of this invention will be mentioned, to assure that the reader fully understands the purpose of the process.

6-hydroxy-2-(4-hydroxyphenyl)-3-[4-(2-dimethylaminoethoxy)benzoyl]benzo[b]thiophene 3-[4-(2-ethylmethylaminoethoxy)benzoyl]-6-hydroxy-2-(4-hydroxyphenyl)benzo[b]thiophene 3-[4-(2-ethylisopropylaminoethoxy)benzoyl]-6-hydroxy-2-(4-hydroxyphenyl)benzo[b]thiophene 3-[4-(2-dibutylaminoethoxy)benzoyl]-6-hydroxy-2-(4-hydroxyphenyl)benzo[b]thiophene 3-[4-[2-(1-methylpropyl)methylaminoethoxy]-benzoyl]-6-hydroxy-2-(4-hydroxyphenyl)benzo[b]thiophene 6-hydroxy-2-(4-hydroxyphenyl)-3-[4-[2-di(2-methylpropyl)aminoethoxy]benzoyl]benzo[b]thiophene 6-hydroxy-2-(4-hydroxyphenyl)-3-[4-(2-pyrrolidinoethoxy)benzoyl]benzo[b]thiophene 6-hydroxy-2-(4-hydroxyphenyl)-3-[4-(2-piperidinoethoxy)benzoyl]benzo[b]thiophene 6-hydroxy-2-(4-hydroxyphenyl)-3-[4-(2-morpholinoethoxy)benzoyl]benzo[b]thiophene 3-[4-(2-hexamethyleneiminoethoxy)benzoyl]-6-hydroxy-2-(4-hydroxyphenyl)benzo[b]thiophene The process of this invention is preferably used for preparing compounds of the above formula wherein $R^1$ and $R^2$ combine to form tetramethylene or pentamethylene.

The acylation step of the present process is a preferred embodiment of the invention.

The compounds of this invention are made by acylating the starting protected dihydroxybenzothiophene with the acylating agent described above, and removing the protecting groups. The manner in which the protected starting compounds are obtained will be discussed first, and then the acylating process, the acylating agents, and the deprotection process will be discussed individually.

The usual ultimate starting compound is 6-hydroxy-2-(4-hydroxyphenyl)benzo[b]thiophene. A synthesis of it is shown below in a preparation.

PROTECTION

The preliminary step in the synthesis is to protect the hydroxy groups, as indicated below.

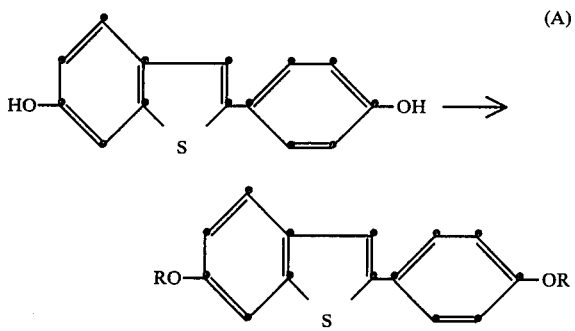

The $—COR^3$ and $—SO_2R^3$ groups are placed on the dihydroxy compound according to methods known in the art. For example, when a $—COR^3$ group is desired, the dihydroxy compound is reacted with an agent such as an acyl chloride, bromide, cyanide or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine or the like. The reaction may also be carried out in an inert solvent such as ethyl acetate, dimethylformamide, dimethylsulfoxide, dioxane, dimethoxyethane, acetonitrile, acetone, methyl ethyl ketone or the like, to which at least one equivalent of an acid scavenger, such as a tertiary amine, has been added. Acylation catalysts such as 4-dimethylaminopyridine or 4-pyrrolidinopyridine may be used, if desired. See, in general, Haslam, *Tetrahedron* 36, 2409-33 (1980). The acylation reactions which provide $—COR^3$ groups are carried out at moderate temperatures in the range of from $-25°$ to $100°$.

Such acylations of the hydroxy groups may also be performed by acid-catalyzed reactions of the appropriate carboxylic acids, in inert organic solvents or neat. Acid catalysts such as sulfuric acid, polyphosphoric acid, methanesulfonic acid and the like are used.

The $—COR^3$ groups may also be provided by forming an active ester of the appropriate acid, such as the esters formed by such known reagents as dicyclohexylcarbodiimide, acylimidazoles, nitrophenols, pentachlorophenol, N-hydroxysuccinimide and 1-hydroxybenzotriazole. See, for example, *Bul. Chem. Soc. Japan* 38, 1979 (1965), and *Chem. Ber.*, 788 and 2024 (1970).

Other techniques are also known, such as by means of mixed anhydrides of the phosphorus compounds, Shioiri and Hamada, *J. Org. Chem.* 43, 3631-32 (1978); the use of 2-haloheterocyclic compounds such as 2-chloropyridine, Narasaka et al., *Chem. Let.*, 763-66 (1977); and the use of thiol esters.

All of the above techniques which provide $—COR^3$ groups are carried out in solvents as discussed above. Those techniques which do not produce an acid product in the course of the reaction, of course, do not call for an acid scavenger in the reaction mixture.

Still other methods are also useful, such as the use of an $R^3$-substituted ketene in an inert solvent, as discussed above, at a low temperature in the range of $-30°$ to $25°$. Still further, the dihydroxy compound can be first converted to its dianion by treatment with a very strong base such as sodium hydroxide, sodium methoxide, potassium hydride, sodium hydride, n-butyllithium or the like, in order to obtain more complete reaction with the reagents which have been mentioned above. Protection by the dianion technique is carried out in an inert solvent as described above, with no additional base or catalyst. The temperature of reactions according to the dianion technique is from $-30°$ to $50°$ C.

When a $—SO_2R^3$-protected compound is desired, the dihydroxy starting compound is reacted with, for example, a derivative of the appropriate sulfonic acid, such as a sulfonyl chloride, bromide or sulfonyl ammonium salt, as taught by King and Manoir, *J. Am. Chem. Soc.* 97, 2566-67 (1975). The dihydroxy compound can also be reacted with the appropriate sulfonic anhydride. Such reactions are carried out under conditions such as were explained above in the discussion of reactions with acyl halides and the like.

The $—SO_2R^3$ groups may also be provided by reaction of the dihydroxy compound with an appropriately substituted sulfene under conditions as discussed above for reactions with substituted ketenes. Still further, any of the sulfonate-producing reactions may be carried out on a dihydroxy compound in the dianion form, as discussed above.

The preferred protected starting compounds are those wherein the protecting group, R, is methanesulfonyl, p-toluenesulfonyl, acetyl, benzoyl, p-anisoyl and benzenesulfonyl. Other classes of preferred protecting groups include those wherein R is $COR^3$; wherein R is $—SO_2R^3$; wherein $R^3$ is $C_1-C_4$ primary or secondary alkyl; and wherein $R^3$ is phenyl, p-tolyl, p-anisyl or mono- or di(halo or nitro)phenyl.

ACYLATION

The acylation of the protected starting compound can be done either with an acylating agent already containing the aminoethoxy group of the desired product, or with a precursor of it, as shown below.

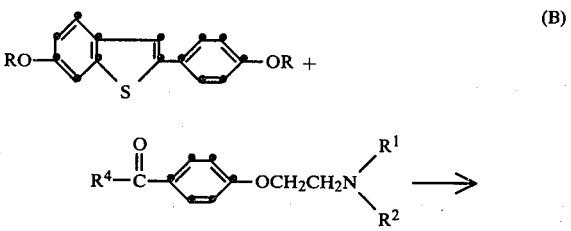

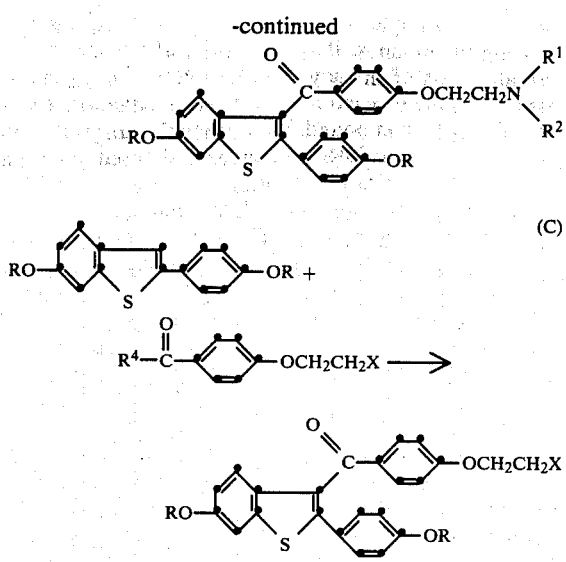

The acylating agents are discussed in detail below.

The acylation of reactions B and C is a Friedel-Crafts acylation, and is carried out in the usual way. Either a Lewis acid or a proton acid may be used as the Friedel-Crafts catalyst; an excellent discussion of such catalysts appears in Olah, Friedel-Crafts and Related Reactions, Interscience Publ., New York, London and Sidney, 1963, vol. I, Ch. III and IV.

As explained by Olah, the classical Friedel-Crafts catalysts were Lewis acids. Such metal halides as aluminum chloride, aluminum bromide, zinc chloride, boron trifluoride, boron trichloride, boron tribromide, titanium tetrachloride, titanium tetrabromide, stannic chloride, stannic bromide, bismuth trichloride and ferric chloride are well known catalysts and are useful in this acylation, especially for acylations of reaction B. The proton acid catalysts are also useful for this acylation, especially for acylations of reaction C, and include such substances as phosphoric acid, polyphosphoric acid, perchloric acid, chlorosulfonic acid, alkylsulfonic acids such as methanesulfonic and ethanesulfonic acids, toluenesulfonic and benzenesulfonic acids, sulfuric acid, chloroacetic acid and trifluoroacetic acid. It is preferred to carry out the acylation with aluminum chloride or trifluoromethanesulfonic acid.

The acylation is ordinarily carried out in a solvent, and any inert organic solvent which is not significantly attacked by the conditions may be used. For example, halogenated solvents such as dichloromethane, 1,2-dichloroethane, chloroform and the like may be used, as can aromatics such as benzene, chlorobenzene and the like, alkanes such as petroleum ether, hexane and the like, and nitrohydrocarbons such as nitrobenzene and nitroalkanes.

It has been found that toluene is rather easily acylated under the conditions used in the Friedel-Crafts acylation step, and so it is important, when toluene is used in an earlier step of the process, to remove it as completely as possible from the protected starting compound, to avoid wasting the acylating agent.

The acylations may be carried out at temperatures from about the ambient temperature to about 100°, preferably at the reflux temperature of the reaction mixture for processes catalyzed by the preferred proton acid catalyst, trifluoromethanesulfonic acid, and preferably at about ambient temperature for Lewis acid catalyzed processes.

The acylating agent is an active form of the appropriate benzoic acid, wherein $R^4$ is one of the recognized "active groups", such as a chlorine atom, a bromine atom, or an activating ester. Appropriate activating esters are formed with hydroxybenzotriazole, acylimidazoles, nitrophenols, pentachlorophenol, N-hydroxysuccinimide, dicyclohexylcarbodiimide and the like. The group $R^4$ may also indicate an anhydride, especially a mixed anhydride such as those formed with small carboxylic acids such as acetic acid, formic acid and especially sulfonic acids.

The preferred acylating agents are these wherein $R^4$ is chloro or bromo. Thus, the most highly preferred individual acylating agents are 4-(2-piperidinoethoxy)benzoyl chloride, 4-(2-piperidinoethoxy)benzoyl bromide, 4-(2-pyrrolidinoethoxy)benzoyl chloride, 4-(2-pyrrolidinoethoxy)benzoyl bromide, 4-[2-(3-methylpyrrolidino)ethoxy]benzoyl chloride and 4-[2-(3-methylpyrrolidino)ethoxy]benzoyl bromide.

It is preferred, when the basic side chain is added according to reaction B above, to use as the acylating agent a small excess (1.05–1.5 molar) of the proper benzoyl halide, and to use, as the Friedel-Crafts catalyst, a slight molar excess of trifluoromethanesulfonic acid, or, alternatively, fluorosulfonic acid, p-toluenesulfonic acid, a dihalophosphoric acid or concentrated sulfuric acid. Alternatively, the reaction is also carried out in a preferred manner by using a substantial excess (1.5 to 3.5 molar) of the benzoyl halide in the presence of a large excess (2–12 molar) of aluminum chloride; other Lewis acid catalysts, such as aluminum bromide and the like may also be used.

In the case of acylations according to reaction C above, it is preferred to carry out the acylation in the presence of a strong acid such as was discussed immediately above. In this reaction, a full equivalent of acid is not necessary; a catalytic amount of acid is adequate. It is preferred to carry out the acylation steps in an inert halogenated solvent such as chloroform, dichloromethane, benzene, 1,2-dichloroethane and the like. In general, see as to such acylation reactions an article by Effenberger, *Angew. Chem. Int. Ed. Engl.* 19, 151–230, especially 163–65 (1980).

DISPLACEMENT

When the starting compound is acylated according to reaction C above, the amino group of the product is subsequently put in place by displacing the X group with the appropriate secondary amine. The X groups are leaving groups, preferably chloro or bromo, which are easily displaced by an amine according to known methods.

For example, the displacement is carried out in an inert solvent such as ketones in the nature of acetone or methyl ethyl ketone, esters such as ethyl acetate and propyl formate, alcohols such as methanol or ethanol, nitriles such as acetonitrile, or amides such as dimethylacetamide and dimethylformamide, or in such inert solvents as hexamethylphosphoramide, and in the presence of an acid scavenger such as alkali metal carbonates and bicarbonates and the like. At least an equimolar quantity of acid scavenger is needed, and preferably a moderate excess. The displacement is carried out at ambient temperature, or may be carried out at moderately elevated temperatures from about ambient temperature to the reflux temperature of the reaction mixture.

More preferably, the displacement may be carried out in the additional presence of a catalytic amount of iodide ion, which acts as a catalyst for the displacement. When iodide is used in the mixture, the temperature range is lower, from about 0° to, preferably, the ambient temperature, although elevated temperatures are possible in some instances.

Further, the anion of the amine may be formed before the reaction is carried out, as by contact with a very strong base such as sodium hydride or an alkyl-lithium compound. The use of an anion does not otherwise change the manner in which the displacement is carried out, except that an acid scavenger is not needed.

DEPROTECTION

A dihydroxy compound is obtained according to this invention by cleaving the protecting groups, R, from the acylated compounds. Both —COR$^3$ and —SOR$^3$— protected compounds have been deprotected by simple hydrolysis with strong or moderately strong bases. For example, bases such as alkali metal hydroxides may be used for the hydrolysis, at temperatures from about the ambient tempeature to about 100°. At least two equivalents of base are needed, of course. Such hydrolyses are conveniently carried out in hydroxylic solvents, especially aqueous alkanols. The reactions may be also carried out, however, in any convenient solvent which lends itself to hydrolysis reactions, such as polyols including ethylene glycol, ethers such as tetrahydrofuran and the like, ketones such as acetone and methyl ethyl ketone and other polar water-miscible solvents such as dimethylsulfoxide. A preferred solvent system is a mixture of methanol and tetrahydrofuran, at ambient temperature. The cleavage may also be carried out with other bases, including, for example, sodium methoxide, potassium t-butoxide, hydrazine, hydroxylamine, ammonia, alkali metal amides and secondary amines such as diethylamine and the like. In some instances, when very strong bases are used, reaction temperatures in the range of from about 0° to the ambient temperature will give adequately rapid reaction rates.

The hydrolysis step lends itself well to reaction with the base in a 2-phase system with the assistance of a phase transfer catalyst. Such catalysts are now well known and are found among the tetraalkyl ammonium halides and among the crown ethers, such as dicyclohexyl-18-crown-6 ether.

In the case of compounds protected with —COR$^3$ groups, hydrolysis is also readily carried out with acid catalysts, such as methanesulfonic acid, hydrochloric acid, hydrobromic acid, sulfuric acid, a mixture of hydrobromic acid/acetic acid, or with acidic ion exchange resins. Such acid-catalyzed hydrolyses are carried out in hydroxylic solvents, such as water, alkanols, aqueous alkanols, or a mixture of tetrahydrofuran/methanol. It is preferred to carry out such hydrolyses at about the reflux temperature of the mixture, but, when particularly strong acids are used, temperatures as low as the ambient temperature are efficient.

All of the above reaction steps give acceptable yields when the stoichiometric amounts of the reactants are used, except as noted in certain specific steps above. As is normally the case in organic chemistry, improved yields are given by the use of an excess amount of one of the reactants, and it is practical to use an excess amount of the cheaper or the more easily obtained reactant. For example, in the formation of the protected starting compounds, it is practical and economical to use an excess of the acylating or sulfonating agent, to assure complete reaction of the more expensive dihydroxy starting compound. Excesses in the range of from about 1% to about 25% are conveniently used, when an excess of one reactant is desired.

The compounds are very often administered in the form of acid addition salts. The salts are conveniently formed, as is usual in organic chemistry, by reacting the compound prepared according to this invention with a suitable acid. The salts are quickly formed in high yields at moderate temperatures, and often are prepared by merely isolating the compound from a suitable acidic wash as the final step of the synthesis. For example, salts may be formed with inorganic or organic acids such as hydrobromic acid, hydriodic acid, sulfonic acids including such agents as naphthalenesulfonic, methanesulfonic and toluenesulfonic acids, sulfuric acid, nitric acid, phosphoric acid, tartaric acid, pyrosulfuric acid, metaphosphoric acid, succinic acid, formic acid, phthalic acid, lactic acid and the like, most preferably with hydrochloric acid, citric acid, benzoic acid, maleic acid, acetic acid or propionic acid. The salt-forming acid is dissolved in an appropriate organic solvent, or aqueous organic solvent, such as an alkanol, ketone or ester for this purpose. A preferred technique for preparing hydrochlorides is to dissolve the free base in a suitable solvent and bubble hydrogen chloride gas through it.

The following preparations and examples further illustrate the process of this invention. Many of the products were identified by nuclear magnetic resonance (mnr) analysis. Such analyses were run at 100 mHz in deuterochloroform unless stated otherwise. The first preparation shows the synthesis of the dihydroxy ultimate starting compound.

PREPARATION 1

6-hydroxy-2-(4-hydroxyphenyl)benzo[b]thiophene

A 100 g. portion of 3-methoxybenzenethiol and 39.1 g. of potassium hydroxide dissolved in 300 ml. of water were added to 750 ml. of denatured ethanol, and the flask was put in a cooling bath. A total of 164 g. of α-bromo-4-methoxyacetophenone was then added in small portions, and the mixture was stirred for 10 minutes in the cooling bath after the addition was complete and then for 3 hours at ambient temperature. The solvent was then evaporated off in vacuum, and 200 ml. of water was added. The mixture was extracted with ethyl acetate, and the organic layer was washed twice with water, twice with aqueous sodium bicarbonate solution, and twice with aqueous sodium chloride solution. The organic layer was then dried over magnesium sulfate, filtered and evaporated under vacuum to obtain 202 g. of crude α-(3-methoxyphenylthio)-4-methoxyacetophenone, which was recrystallized from methanol and washed with hexane to obtain 158 g. of purified product, m.p. 53°.

A 124 g. portion of the above intermediate was added in small portions to 930 g. of polyphosphoric acid at 85°. The temperature rose to 95° during the addition, and the mixture was stirred at 90° for 30 minutes after the addition was complete, and was then stirred an additional 45 minutes while it cooled without external heating. One liter of crushed ice was then added to the mixture, and an external ice bath was applied to control the temperature while the ice melted and diluted the acid. Five hundred ml. of additional water was added, and the light pink precipitate was filtered off and washed, first with water and then with methanol. The solids were dried under vacuum at 40° to obtain 119 g. of crude 6-methoxy-2-(4-methoxyphenyl)benzo[b]thiophene. The crude product was slurried in hot methanol, filtered, and washed with cold methanol, and the solids were recrystallized from 4 liters of ethyl acetate, filtered, washed with hexane and dried to obtain 68 g. of purified intermediate product, m.p. 187°–190.5°.

Ninety g. of pyridine hydrochloride was added to a flask equipped with a distillation head, condenser and collecting flask, and was heated with stirring until the temperature in the distillation head was 220°. The distillation apparatus was then removed, the pot was cooled to 210°, and 30 g. of the above-prepared dimethoxy intermediate was added. The mixture was stirred at 210° for 30 minutes, and was then poured into 250 ml. of ice-water. The precipitate was extracted into 500 ml. of ethyl acetate, and the organic layer was washed with 150 ml. of saturated aqueous sodium bicarbonate and then with 150 ml. of saturated aqueous sodium chloride. The organic layer was then dried over magnesium sulfate, filtered and evaporated to dryness under vacuum to obtain 25.5 g. of the desired intermediate product, m.p. >260°.

The next group of preparations illustrate the synthesis of protected starting compounds having various R groups.

PREPARATION 2

6-acetoxy-2-(4-acetoxyphenyl)benzo[b]thiophene

Forty g. of 6-hydroxy-2-(4-hydroxyphenyl)benzo[b]thiophene was dissolved in 800 ml. of anhydrous pyridine, and 41.6 g. of acetic anhydride and 100 mg. of 4-dimethylaminopyridine were added. The mixture was allowed to stand overnight at ambient temperature, and was then evaporated to an oily residue under vacuum. The residue was slurried with 3 liters of water with vigorous stirring, and the crystals which precipitated were collected by filtration and washed thoroughly with water. The solids were then dried at 80° under vacuum to obtain 52.5 g. of the acetyl-protected intermediate, m.p. 208°–210°.

PREPARATION 3

6-benzoyloxy-2-(4-benzoyloxyphenyl)benzo-[b]thiophene

The synthesis was carried out exactly according to the process of Preparation 2, except that 51.1 g. of benzoyl chloride was used instead of acetic anhydride. The product was 73.7 g. of the expected benzoyl-protected intermediate product in the form of white crystals, m.p. 216°–218°.

PREPARATION 4

6-methanesulfonyloxy-2-(4-methanesulfonyloxyphenyl)benzo[b]thiophene

Twenty g. of 6-hydroxy-2-(4-hydroxyphenyl)benzo[b]thiophene was dissolved in 400 ml. of pyridine, together with 23.4 g. of methanesulfonyl chloride and 50 mg. of 4-dimethylaminopyridine. The mixture was stirred under a nitrogen blanket overnight at ambient temperature, and was then poured into 2 liters of water and stirred vigorously. The solids were collected by filtration, and washed successively with water, methanol and diethyl ether. The washed solids were then vacuum dried at 60° to obtain 32.5 g. of the desired intermediate product, m.p. 195°–197°.

PREPARATION 5

6-benzenesulfonyloxy-2-(4-benzenesulfonyloxyphenyl)-benzo[b]thiophene

The synthesis was carried out substantially according to Preparation 2 above, except that 64.1 g. of benzenesulfonyl chloride was used in place of acetic anhydride. The product was worked up as described in Preparation 2 to obtain 85 g. of the crude product, m.p. 138°–139°, which was recrystallized twice from ¼ methanol/ethyl acetate to obtain purified intermediate product, m.p. 146°–148°.

The following group of examples illustrates the acylation step of the process of this invention.

EXAMPLE 1

6-acetoxy-2-(4-acetoxyphenyl)-3-[4-(2-pyrrolidinoethoxy)benzoyl]benzo[b]thiophene, hydrochloride A 25 g. portion of 4-(2-pyrrolidinoethoxy)-benzoic acid, hydrochloride, was converted to its acid chloride by dissolving it in 200 ml. of 1,2-dichloroethane and adding one drop of dimethylformamide and 36.5 g. of thionyl chloride. The mixture was stirred under reflux under a nitrogen blanket for two hours, and was then evaporated under vacuum to obtain the tan-white acid chloride.

To the acid chloride were added 1 liter of 1,2-dichloroethane, 20 g. of 6-acetoxy-2-(4-acetoxyphenyl)-benzo[b]thiophene and 73.4 g. of aluminum chloride, which last was added over a period of about 3 minutes with vigorous stirring. The mixture was then stirred for one hour, and was poured over 1 liter of ice-water. The layers were separated, and the aqueous layer was extracted three times with 200 ml. portions of warm chloroform. The organic layers were combined, dried over magnesium sulfate, filtered and evaporated under vacuum to obtain a yellow oil which was not further purified.

EXAMPLE 2

6-benzoyloxy-2-(4-benzoyloxyphenyl)-3-[4-(2-pyrrolidinoethoxy)benzoyl]benzo[b]thiophene, hydrochloride An acid chloride was formed from 18.1 g. of 4-(2-pyrrolidinoethoxy)benzoic acid, hydrochloride, as described in Example 1. The acid chloride was used to acylate 20 g. of 6-benzoyloxy-2-(4-benzoyloxyphenyl)-benzo[b]thiophene as described above in Example 1, using 53.2 g. of aluminum chloride. A sample of the impure product, a tan foam, was recrystallized from denatured ethanol to obtain an analytical sample, m.p. 218°–222°.

EXAMPLE 3

6-methanesulfonyloxy-2-(4-methanesulfonyloxyphenyl)-3-[4-(2-pyrrolidinoethoxy)benzoyl]benzo[b]thiophene, hydrochloride The acid chloride of 20.4 g. of 4-(2-pyrrolidinoethoxy)benzoic acid, hydrochloride was prepared as described in Example 1, and was used to acylate 20 g. of 6-methanesulfonyloxy-2-(4-methanesulfonyloxyphenyl)benzo[b]thiophene as described in Example 1, except that the amount of aluminum chloride was 60 g., of which 30 g. was added initially, and the rest was added in 10 g. portions at 15 minute intervals. The reaction mixture was stirred for 16 hours, and was worked up as described in Example 1 to obtain an oil, which was crystallized from denatured ethanol to obtain 27.5 g. of purified product, m.p. 196°–199°. A 4 g. sample was purified further by chromatography to obtain an analytical sample, m.p. 207°–207.5°.

EXAMPLE 4

6-methanesulfonyloxy-2-(4-methanesulfonyloxyphenyl)-3-[4-(2-dimethylaminoethoxy)benzoyl]benzo[b]-thiophene, hydrochloride The acid chloride was prepared from 8.8 g. of 4-(2-dimethylaminoethoxy)benzoic acid, hydrochloride, as described in Example 1, and to the acid chloride was added 4 g. of 6-methanesulfonyloxy-2-(4-methanesulfonyloxyphenyl)benzo[b]thiophene, 150 ml. of 1,2-dichloroethane and 14.4 g. of aluminum chloride, of which 4.8 g. was added first, and 3.2 g. portions were added every 15 minutes thereafter. The reaction mixture was poured over ice only 45 minutes after the last addition of aluminum chloride. A precipitate formed in the water-halocarbon mixture, which was collected by filtration and air dried to obtain 6.2 g. of impure product, which was recrystallized from 90 ml. of methanol to obtain 5.4 g. of purified product, m.p. 204°–206°.

EXAMPLE 5

6-methanesulfonyloxy-2-(4-methanesulfonyloxyphenyl)-3-[4-(2-hexamethyleneiminoethoxy)benzoyl]-benzo[b]thiophene, hydrochloride The acid chloride of 5.6 g. of 4-(2-hexamethyleneiminoethoxy)benzoic acid, hydrochloride, was prepared as described in Example 1, except that the solvent was 50 ml. of toluene. To the acid chloride was added 150 ml. of 1,2-dichloroethane, 5 g. of 6-methanesulfonyloxy-2-(4-methanesulfonyloxyphenyl)benzo[b]thiophene, and 13.4 g. of aluminum chloride. The mixture was stirred for 30 minutes, and an additional 1.7 g. of aluminum chloride was added. After 15 minutes of additional stirring, the reaction mixture was poured over ice. The layers were separated, and the aqueous layer was washed twice with 50 ml. portions of chloroform. The organic layers were combined and washed with 25 ml. of aqueous sodium chloride solution. The organic solution was then dried over magnesium sulfate, filtered and evaporated to dryness to obtain 9.5 g. of oil, which was not further purified.

EXAMPLE 6

3-[4-(2-diethylaminoethoxy)benzoyl]-6-methanesulfonyloxy-2-(4-methanesulfonyloxyphenyl)benzo[b]thiophene, hydrochloride A 5.2 g. portion of 4-(2-diethylaminoethoxy)benzoic acid, hydrochloride, was converted to the acid chloride, and used to acylate 5 g. of 6-methanesulfonyloxy-2-(4-methanesulfonyloxyphenyl)benzo[b]thiophene according to the process of Example 5. The amount of aluminum chloride was 15.1 g., and the reaction mixture was stirred for 1.5 hours after its addition. The mixture was worked up as described in Example 5 to obtain a yellow foam, which began to crystallize after standing for several days. It was triturated with denatured ethanol and recrystallized from denatured ethanol to obtain 6.5 g. of purified crystalline product, m.p. 172°–174°.

EXAMPLE 7

3-[4-(2-diisopropylaminoethoxy)benzoyl]-6-methanesulfonyloxy-2-(4-methanesulfonyloxyphenyl)-benzo[b]thiophene, hydrochloride A 7.6 g. portion of 4-(2-diisopropylaminoethoxy)benzoic acid, hydrochloride, was converted to the acid chloride as described in Example 1 above, and was used to acylate 5 g. of 6-methanesulfonyloxy-2-(4-methanesulfonyloxyphenyl)benzo[b]thiophene in the presence of 20 g. of aluminum chloride. Work up according to Example 4 gave 7.4 g. of crystalline product after trituration of the isolated oil with denatured ethanol. The product was recrystallized from denatured ethanol to obtain 6.5 g. of purified product, and a 1.5 g. portion was further purified by chromatography over silica gel, eluting with 1:3 methanol:chloroform to obtain 1.15 g. of analytical sample, m.p. 198°–201°.

EXAMPLE 8

6-methanesulfonyloxy-2-(4-methanesulfonyloxyphenyl)-3-[4-(2-morpholinoethoxy)benzoyl]benzo[b]-thiophene, hydrochloride The process of Example 7 was used to prepare the above product, starting with 7.2 g. of 4-(2-morpholinoethoxy)benzoic acid, hydrochloride, and 5 g. of 6-methanesulfonyloxy-2-(4-methanesulfonyloxyphenyl)-benzo[b]thiophene. A yield of 4.25 g. of recrystallized product was obtained, of which 1.25 g. was purified by chromatography as explained in Example 7 above to obtain 0.9 g. of highly purified product, m.p. 197°–200°.

EXAMPLE 9

6-acetoxy-2-(4-acetoxyphenyl)-3-[4-(2-piperidinoethoxy)benzoyl]benzo[b]thiophene, hydrochloride An acylating agent, in acid chloride form, was prepared by combining 26.3 g. of 4-(2-piperidinoethoxy)-benzoic acid, hydrochloride, 36.5 g. of thionyl chloride and 1 drop of dimethylformamide in 200 ml. of 1,2-dichloroethane, and stirring the mixture under reflux for 2 hours under a nitrogen atmosphere. The mixture was then evaporated to dryness under vacuum to obtain the desired 4-(2-piperidinoethoxy)benzoyl chloride, hydrochloride, which was dissolved in 1 liter of 1,2-dichloroethane. To the solution was added 20 g. of 6-acetoxy-2-(4-acetoxyphenyl)benzo[b]thiophene and the mixture was stirred vigorously. To it was then added, over about 3 minutes, 73.4 g. of aluminum chloride. During the addition, the reaction mixture turned dark brown and hydrogen chloride evolved. The mixture was then stirred for one hour, and was poured over 1 liter of ice-water. The layers were separated, and the aqueous layer was extracted three times with 200 ml. portions of warm chloroform. The organic layers were combined and dried over magnesium sulfate, and were then filtered and evaporated under vacuum to obtain a brownish-yellow oil, which was not purified. The presence of the desired product was confirmed by thin layer chromatography (TLC) on silica gel, eluting with 9/1 chloroform/methanol, which showed that the major constituent ran at the same $R_f$ as authentic 6-acetoxy-2-(4-acetoxyphenyl)-3-[4-(2-piperidinoethoxy)benzoyl]-benzo[b]thiophene.

EXAMPLE 10

6-benzoyloxy-2-(4-benzoyloxyphenyl)-3-[4-(2-piperidinoethoxy)benzoyl]benzo[b]thiophene, hydrochloride The process of this example was run as was the process of Example 9, starting with the acid chloride formed from 18.9 g. of 4-(2-piperidinoethoxy)benzoic acid, hydrochloride, and 20 g. of 6-benzoyloxy-2-(4-benzoyloxyphenyl)benzo[b]thiophene. The reaction mixture was stirred for 1.5 hours, and was then worked up as described in Example 9 to obtain the desired product as an oil. A small portion of the crude product was crystallized from denatured ethanol to provide an analytical sample, m.p. 230°–233°, the identity of which was confirmed by nmr analysis. $\delta$1.30–2.50 (6H, m, NH(CH$_2$CH$_2$)$_2$CH$_2$); 2.50–3.75 (6H, m, NH(CH$_2$CH$_2$)$_2$CH$_2$ and OCH$_2$CH$_2$N); 4.56 (2H, m, OCH$_2$CH$_2$N); 6.77 (2H, d, J=9 Hz, aromatic o to OCH$_2$); 7.10 (2H, d, J=9 Hz, aromatic o to OCO); 7.10–7.90 (17H, m, aromatic); 8.00–8.27 (6H, m, aromatic o to CO); 12.30–12.80 (1H, broad s, NH).

The next two preparations illustrate the acylation of sulfonyl-protected starting compounds.

EXAMPLE 11

6-benzenesulfonyloxy-2-(4-benzenesulfonyloxyphenyl)-3-[4-(2-piperidinoethoxy)benzoyl]benzo[b]thiophene, hydrochloride An acid chloride was formed from 8.21 g. of 4-(2-piperidinoethoxy)benzoic acid, hydrochloride, as described in Example 9, and was combined with 10 g. of 6-benzenesulfonyloxy-2-(4-benzenesulfonyloxyphenyl)benzo[b]thiophene in 500 ml. of 1,2-dichloroethane and treated with 22.9 g. of aluminum chloride. The mixture was stirred at ambient temperature overnight, and worked up as described in Example 9 above. The product was 15 g. of tan foam which would not crystallize. A 1 g. sample of the crude product was purified by column chromatography over a 4×20 cm. silica gel column, eluting first with chloroform, and then with 25% methanol in chloroform. The product-containing fractions were combined, treated with hydrochloric acid to form the hydrochloride salt, and evaporated to dryness under vacuum to provide the product as an oil, the identity of which was confirmed by an absorption maximum at 1645 cm$^{-1}$ in its infrared spectrum, indicative of the —CO— function of the desired product. Its identity was further confirmed by its conversion to 6-hydroxy-2-(4-hydroxyphenyl)-3-[4-(2-piperidinoethoxy)benzoyl]benzo[b]thiophene in Example 28 below.

EXAMPLE 12

6-methanesulfonyloxy-2-(4-methanesulfonyloxyphenyl)-3-[4-(2-piperidinoethoxy)benzoyl]benzo[b]thiophene, hydrochloride The acid chloride was formed from 2.0 g. of 4-(2-piperidinoethoxy)benzoic acid, hydrochloride, as described in Example 9, and was combined with 2 g. of 6-methanesulfonyloxy-2-(4-methanesulfonyloxyphenyl)benzo[b]thiophene in 50 ml. of dichloromethane. A 2.4 g. portion of trifluoromethanesulfonic acid was added, and the mixture was stirred overnight under reflux. The reaction mixture was then poured over ice and sodium bicarbonate solution, and the organic layer was dried over magnesium sulfate and filtered. The filtrate was evaporated under vacuum to a yellow foam, which was treated with excess 3% hydrogen chloride in anhydrous methanol. The mixture was evaporated to dryness under vacuum to obtain a white foam which was dissolved in 18 ml. of boiling methanol. The solution was cooled to obtain 3.1 g. of the desired product, m.p. 128°–130° C., which was identified by nmr analysis. $\delta$1.50–2.00 (6H, m, N-(CH$_2$CH$_2$)$_2$CH$_2$); 2.57–3.75 (6H, m, NH(CH$_2$CH$_2$)$_2$CH$_2$ and OCH$_2$CH$_2$N); 3.36 (3H, s, CH$_3$SO$_2$); 3.46 (3H, s, CH$_3$SO$_2$); 4.45 (2H, broad t, J=6 Hz, OCH$_2$CH$_2$N); 6.97 (2H, d, J=9 Hz, aromatic o to OCH$_2$); 7.25–7.80 (8H, m, aromatic); 8.25 (1H, d, J=2 Hz, aromatic, o to O and S); 10.70–11.00 (1H, broad s, NH). Infrared absorption in KBr for the ketone CO appears at 1640 cm.$^{-1}$. Ultraviolet absorption maxima: $\lambda_{max}$ ($\epsilon$) in ethanol: 273 nm. (sh 26,000), 290 (29,500).

EXAMPLE 13

6-methanesulfonyloxy-2-(4-methanesulfonyloxyphenyl)-3-[4-(2-piperidinoethoxy)benzoyl]benzo[b]thiophene, hydrochloride The acid chloride was prepared from 19.7 g. of 4-(2-piperidinoethoxy)benzoic acid, hydrochloride in 200 ml. of toluene with 44.9 g. of thionyl chloride, and the acid chloride was used to acylate 20 g. of 6-methanesulfonyloxy-2-(4-methanesulfonyloxyphenyl)benzo[b]thiophene in the presence of 59.6 g. of aluminum chloride. The aluminum chloride was added portionwise over a period of 30 minutes, and the reaction mixture was then stirred for 16 hours. It was poured over 2 liters of ice-water, and the product was extracted from the aqueous layer with two 200 ml. portions of warm chloroform. The organics were combined, dried and evaporated to obtain an oil, which was crystallized from 350 ml. of methanol to obtain 28 g. of crude product, m.p. 133°–135°.

The following group of examples illustrate synthesis in which the protecting groups are cleaved from acylated compounds.

EXAMPLE 14

6-hydroxy-2-(4-hydroxyphenyl)-3-[4-(2-pyrrolidinoethoxy)benzoyl]benzo[b]thiophene The 6-acetoxy-2-(4-acetoxyphenyl)-3-[4-(2-pyrrolidinoethoxy)benzoyl]benzo[b]thiophene produced from the acylation of 10 g. of 6-acetoxy-2-(4-acetoxyphenyl)benzo[b]thiophene with the acid chloride produced from 25 g. of 4-(2-pyrrolidinoethoxy)benzoic acid, hydrochloride, was added to 275 ml. of methanol, and 55 ml. of 5 N sodium hydroxide was added. The mixture was stirred under reflux for 45 minutes, and the solvent was then removed under vacuum. The residue was dissolved in 300 ml. of methanol, and was extracted twice with diethyl ether. The ether layers were combined, and backwashed with 1 N sodium hydroxide. The aqueous layers were combined and acidified to pH 2–3, and were then made basic to pH 8. The basic solution was then extracted several times with ethyl acetate, and the organic layers were combined, dried over magnesium sulfate, filtered and evaporated to a solid under vacuum. After vacuum drying at ambient temperature for several hours, the solid weighed 10.4 g. Analysis by nmr spectroscopy indicated that the product was the desired 6-hydroxy-2-(4-hydroxyphenyl)-3-[4-(2-pyrrolidinoethoxy)benzoyl]benzo[b]thiophene but that approximately an equimolar amount of ethyl acetate was also present. Much of the crude product was used in experimentation on crystallization and purification procedures and so no precise total purified yield was determined. A 1.02 g. sample was chromatographed over 8.0 g. of silica gel using 9/1 ethyl acetate/methanol for elution. The column dimensions were 3×27 cm and 50 ml. fractions were collected. Fractions #13 to 27 provided a yellow oil which was dissolved in 30 ml. of 1 N sodium hydroxide and stirred for 15 minutes at ambient temperature. After acidification with 32 ml. of 1 N hydrochloric acid and basification with excess solid sodium bicarbonate, a yellow solid was collected and after vacuum drying overnight it weighed 0.57 g. This material was essentially pure product as judged by nmr and ultraviolet spectral data as well as elemental analysis.

A 1.0 g. portion of the crude product prepared above was chromatographed on a 3×30 cm. column of silica gel, eluting with 1/9 methanol/chloroform. Fifty-ml. samples were collected, and fractions 13–30 were combined and evaporated to dryness to obtain a yellow oil which was dissolved in 30 ml. of 1 N sodium hydroxide. Nitrogen was bubbled through the solution for 15 minutes, and ice and 32 ml. of 1 N hydrochloric acid were added. Then 8 ml. of saturated aqueous sodium bicarbonate was added, and the mixture was stirred for 1 hour and filtered. The solids were washed with water and vacuum dried and a sample was analyzed by 100 mHz nmr in dmso-d$_6$. δ1.72 (4H, m, N(CH$_2$C$\underline{H}_2$)$_2$); 2.68 (4H, m, N(C$\underline{H}_2$CH$_2$)$_2$; 2.94 (2H, t, J=6 Hz, OCH$_2$C$\underline{H}_2$N); 4.15 (2H, t, J=6 Hz, OC$\underline{H}_2$CH$_2$N); 6.68 (2H, d, J=9 Hz, aromatic o to OH); 6.85 (1H, q, J$_{H4-H5}$=9 Hz, J$_{H5-H7}$=2 Hz, H5 of benzothiophene ring); 6.93 (2H, d, J=9 Hz, aromatic o to OCH$_2$CH$_2$N); 7.18 (2H, d, J=9 Hz, aromatic m to OH); 7.25 (1H, d, J=9 Hz, H4 of benzothiophene ring); 7.67 (2H, d, J=9 Hz, aromatic o to CO); 9.75 (2H, broad s, OH).

EXAMPLE 15

6-hydroxy-2-(4-hydroxyphenyl)-3-[4-(2-pyrrolidinoethoxy)benzoyl]benzo[b]thiophene The yellow oil obtained from Example 1 above was dissolved in 700 ml. of methanol, and 100 ml. of 5 N sodium hydroxide was added. The mixture was stirred for 2 hours at ambient temperature, and then the solvent was removed under vacuum. The residue was dissolved in 500 ml. of water and was washed with two 500 ml. portions of diethyl ether. The water layer was acidified to pH 2 with cold methanesulfonic acid, was diluted to about 3 liters, and was washed again with two 1 liter portions of diethyl ether. The aqueous layer was separated, degassed under vacuum, and made basic by cautions addition of sodium bicarbonate. A precipitate developed, and was collected by filtration and washed with water. The solids were vacuum dried at 70° to obtain 13 g. of impure product, which was dissolved in 500 ml. of hot acetone, filtered and evaporated down to approximately 100 ml. volume. The solution was cooled and scratched to obtain 11.3 g. of product, which was identified by nmr, infrared (IR), and ultraviolet (UV) as substantially identical to the products of Examples 14 and 18.

EXAMPLE 16

6-hydroxy-2-(4-hydroxyphenyl)-3-[4-(2-pyrrolidinoethoxy)benzoyl]benzo[b]thiophene To the crude product from Example 2 was added 400 ml. of ethanol, 400 ml. of water and 55 ml. of methanesulfonic acid. The mixture was heated on the steam bath for 72 hours, and the volatile constituents were evaporated under vacuum. The residue was diluted to about 4 liters with water, and the solution was washed in two portions with one liter each of clean diethyl ether. The resulting aqueous layers were combined, degassed under vacuum, and cooled to about 20° by adding ice. The pH was then adjusted to 8.4 by the addition of aqueous ammonia. A yellow solid precipitated, which was collected by filtration and washed with cold water. The solids were dried at 60° to constant weight, 18.8 g., and were recrystallized from acetone to obtain 16.3 g. of purified product which was positively identified by nmr, IR and UV spectra as substantially identical to the products of Example 14 and 18.

EXAMPLE 17

6-hydroxy-2-(4-hydroxyphenyl)-3-[4-(2-pyrrolidinoethoxy)benzoyl]benzo[b]thiophene A 5 g. portion of 6-methanesulfonyloxy-2-(4-methanesulfonyloxyphenyl)-3-[4-(2-pyrrolidinoethoxy)benzoyl]benzo[b]thiophene, hydrochloride, was dissolved in 125 ml. of denatured ethanol and 15 ml. of 5 N sodium hydroxide, and the mixture was stirred under reflux for one hour. The ethanol was then evaporated away under vacuum, and the residue was dissolved in water. The mixture was then made acid with 1 N hydrochloric acid, and was then made basic with sodium bicarbonate. The basic solution was extracted three times with 100 ml. portions of ethyl acetate, dried over magnesium sulfate, filtered and evaporated to an oil, 3.6 g., under vacuum. The oil was shown by thin layer chromatography to contain the desired product by comparison with authentic samples. It was purified further by chromatography on silica gel by elution with 6% methanol in chloroform. The size of the column was 3.5×2.5 cm., and 20 ml. fractions were collected. Fractions 31 through 150 contained 2.4 g. of partially purified product, which was identified by thin layer chromatographic comparison with an authentic sample of the desired product.

EXAMPLE 18

6-hydroxy-2-(4-hydroxyphenyl)-3-[4-(2-pyrrolidinoethoxy)benzoyl]benzo[b]thiophene A 23.8 g. portion of the product of Example 3 above was added to 600 ml. of tetrahydrofuran, 240 ml. of methanol and 40 ml. of 5 N sodium hydroxide. The mixture was stirred at ambient temperature for 60 hours, and then it was evaporated under vacuum. The residue was diluted to 400 ml. with water, and the solution was continuously extracted with diethyl ether for 8 hours. The aqueous phase was then filtered, cooled to below 10°, and acidified to pH 2 with methanesulfonic acid. It was then diluted to about 7 liters with water, and was extracted with diethyl ether. The aqueous layer was degassed under vacuum and made basic with sodium bicarbonate. The solids which precipitated were collected and vacuum dried, and purified by column chromatography on a 4.5×60 cm. column of silica gel, using as eluant a gradient composed of 2 liters of 1% methanol in chloroform phasing to 2 liters of 25% methanol in chloroform. Twenty ml. fractions were collected, and fractions 33 through 150 gave 13.5 g. of product, m.p. 146°–147° after crystallization from acetone. Its UV spectrum showed an absorption maximum at 290 nm. (32,500). The IR spectrum showed a maximum at 1607 cm.$^{-1}$ attributable to the conjugated eneone system.

EXAMPLE 19

3-[4-(2-dimethylaminoethoxy)benzoyl]-6-hydroxy-2-(4-hydroxyphenyl)benzo[b]thiophene Two g. of the product of Example 4 above was dissolved in 100 ml. of denatured ethanol and 5 ml. of 5 N sodium hydroxide, and the solution was stirred under reflux under nitrogen for 1.5 hours. The mixture was then evaporated under vacuum to remove most of the methanol, and the residue was dissolved in 200 ml. of water and washed with 300 ml. of diethyl ether. The aqueous layer was degassed, and nitrogen was bubbled through it to remove all traces of ether. The mixture was then made acid with 1 N hydrochloric acid, and was then made basic with excess sodium bicarbonate. The yellow solids were collected, washed with cold water and dried to obtain 1.21 g. of crude product. A 2×30 cm. column of silica gel was prepared, and the crude product was purified on it by elution with 1:9 methanol:chloroform. The product eluted after the impurities, and was collected by evaporation of the product-containing fractions as a yellow oil. Crystallization from acetone and recrystallization from acetone gave 0.64 g. of the desired product, m.p. 141°–144°, which was further identified by its nmr spectrum: (taken in dmso-d$_6$ at 100 mHz) $\delta$ 2.17 (6H, s, NCH$_3$); 2.57 (2H, t, J=6 Hz, NCH$_2$); 4.05 (2H, t, J=6 Hz, OCH$_2$); 6.66 (2H, d, J=9 Hz, aromatic o to OH); 6.85 (1H, q, J$_{H4-H5}$=9 Hz, J$_{H5-H7}$=2 Hz, H5 of benzothiophene ring); 6.90 (2H, d, J=9 Hz, aromatic o to OCH$_2$); 7.18 (2H, d, J=9 Hz, aromatic m to OH); 7.26 (1H, d, J=9 Hz, H4 of benzothiophene ring); 7.34 (1H, d, J=2 Hz, H7 of benzothiophene ring); 7.65 (2H, d, J=9 Hz, aromatic o to CO); 9.73 (2H, broad s, OH). Ultraviolet spectrum $\lambda_{max}$ ($\epsilon$) in ethanol: 290 nm (32,500); infrared absorption in KBr at 1608 cm$^{-1}$, attributable to the eneone system, and a molecular ion in the electron impact mass spectrum at m/e 433 (calculated for C$_{25}$H$_{23}$NO$_4$S: 433).

EXAMPLE 20

3-[4-(2-hexamethyleneiminoethoxy)benzoyl]-6-hydroxy-2-(4-hydroxyphenyl)benzo[b]thiophene The process of Example 19 was used again to hydrolyze 9.0 g. of the product of Example 5 above. The crude product was 5.2 g. of a yellow solid, which was purified by chromatography as described in Example 19, except that a gradient solvent composed of 1.5 liters of 5% methanol in chloroform phasing to 1.5 liters of 10% methanol in chloroform was used. Twenty ml. fractions were collected, and fractions 78–100 gave 2.45 g. of a yellow foam which was identified as the expected product by its nmr spectrum (taken in dmso-d$_6$ at 100 mHz): $\delta$1.53 (8H, s, N(CH$_2$CH$_2$CH$_2$); 2.65 (4H, m, N(CH$_2$CH$_2$CH$_2$)$_2$); 2.81 (2H, t, J=6 Hz, NCH$_2$CH$_2$O); 4.04 (2H, t, J=6 Hz, NCH$_2$CH$_2$O); 6.68 (2H, d, J=9 Hz, aromatic o to OH); 6.85 (1H, q, J$_{H4-H5}$=9 Hz, J$_{H5-H7}$=2 Hz, H5 of benzothiophene ring); 6.90 (2H, d, J=9 Hz, aromatic o to OCH$_2$; 7.18 (2H, d, J=9 Hz, aromatic m to OH); 7.26 (1H, d, J=9 Hz, H4 of benzothiophene ring); 7.34 (1H, d, J=2 Hz, H7 of benzothiophene ring); 7.66 (2H, d, J=9 Hz, aromatic o to CO); 9.71 (2H, broad s, OH). High resolution mass spectrum: calculated for C$_{29}$H$_{29}$NO$_4$S 487.18172, found 487.18070. Ultraviolet spectrum $\lambda_{max}$ ($\epsilon$) taken in ethanol 290 nm (32,500); infrared absorption in KBr at 1608 cm$^{-1}$ attributable to the eneone system.

EXAMPLE 21

3-[4-(2-diethylaminoethoxy)benzoyl]-6-hydroxy-2-(4-hydroxyphenyl)benzo[b]thiophene A 4 g. portion of the product of Example 6 above was added to 100 ml. of tetrahydrofuran, 40 ml. of methanol and 10 ml. of 5 N sodium hydroxide, and the mixture was stirred at ambient temperature for 24 hours. The volatile portions were then evaporated under vacuum, and the product was worked up as described above in Example 19. The yellow solid obtained was dried, and was purified by chromatography as described above in Example 20. The process gave 2.0 g. of a yellow foam, which was identified as the expected product by its nmr spectrum (taken in dmso-d$_6$ at 100 mHz): $\delta$0.93 (6H, t, J=7 Hz, CH$_2$CH$_3$); 2.50 (4H, q, J=7 Hz, CH$_2$CH$_3$); 2.72 (2H, t, J=6 Hz, NCH$_2$); 4.01 (2H, t, J=6 Hz, OCH$_2$CH$_2$N); 6.67 (2H, d, J=9 Hz aromatic o to OH); 6.85 (1H, q, J$_{H4-H5}$=9 Hz, J$_{H5-H7}$=2 Hz, H5 of benzothiophene ring); 6.88 (2H, d, J=9 Hz, aromatic o to OCH$_2$); 7.18 (2H, d, J=9 Hz, aromatic m to OH); 7.27 (1H, d, J=9 Hz, H4 of benzothiophene ring); 7.34 (1H, d, J=2 Hz, H7 of benzothiophene ring); 7.66 (2H, d, J=9 Hz, aromatic o to CO); 9.72 (2H, broad s, OH). High resolution mass spectrum: calculated for C$_{27}$H$_{27}$NO$_4$S: 461.16607, found 461.16551; Ultraviolet spectrum $\lambda_{max}$ ($\epsilon$) taken in ethanol 290 cm (34,000); infrared absorption in KBr at 1608 cm$^{-1}$ attributable to the eneone system.

EXAMPLE 22

3-[4-(2-diisopropylaminoethoxy)benzoyl]-6-hydroxy-2-(4-hydroxyphenyl)benzo[b]thiophene A 5 g. portion of the product of Example 7 above was hydrolyzed as described above in Example 21, and the residue obtained after evaporation of the volatiles was dissolved in 300 ml. of water. Then solution was washed with 150 ml. of 15:1 diethyl ether:ethyl acetate, and was then made acid with methanesulfonic acid. The solution was then washed with 200 ml. of diethyl ether, and was degassed under vacuum and then made basic with sodium bicarbonate. The solids were collected, washed and vacuum dried to obtain 3.2 g. of crude product. The crude product was chromatographed over a 1 inch×24 inch silica gel column, eluting with a gradient composed of 2 liters of 2% methanol in chloroform phasing into 2 liters of 20% methanol in chloroform. The product-containing fractions were combined and evaporated to dryness to obtain 2.5 g. of purified product, which was characterized by its nmr spectrum (taken in dmso-d$_6$ at 100 mHz): $\delta$0.96 (12H, d, J=7 Hz, (CH(CH$_3$)$_2$)$_2$; 2.72 (2H, t, J=6 Hz, NCH$_2$); 2.96 (2H, m, J=7 Hz, (CH(CH$_3$)$_2$)$_2$); 3.88 (2H, t, J=6 Hz, OCH$_2$); 6.65 (2H, d, J=9 Hz, aromatic o to OH); 6.83 (1H, q, J$_{H4-H5}$=9 Hz, J$_{H5-H7}$=2 Hz, H5 of benzothiophene ring); 6.87 (2H, d, J=9 Hz, aromatic o to OCH$_2$); 7.15 (2H, d, J=9 Hz, aromatic m to OH); 7.26 (1H, d, J=9 Hz, H4 of benzothiophene ring); 7.32 (1H, d, J=2 Hz, H7 of benzothiophene ring); 7.64 (2H, d, J=9 Hz, aromatic o to CO); 9.70 (2H, broad s, OH). High resolution mass spectrum: calculated for C$_{29}$H$_{31}$NO$_4$S: 489.199, found 489.199; Ultraviolet spectrum $\lambda_{max}$ ($\epsilon$) taken in ethanol 290 nm. (32,000); infrared absorption in KBr at 1605 cm$^{-1}$ attributable to the eneone system.

EXAMPLE 23

6-hydroxy-2-(4-hydroxyphenyl)-3-[4-(2-morpholinoethoxy)benzoyl]benzo[b]thiophene Three g. of the product of Example 8 above was hydrolyzed, worked up and chromatographed as described in Example 22 above to obtain 1.95 g. of a yellow foam, which did not crystallize, but was identified as the expected product by its nmr spectrum (taken in dmso-d$_6$ at 100 mHz): δ2.42 (4H, m, N(CH$_2$CH$_2$)$_2$O); 2.64 (2H, t, J=6 Hz, NCH$_2$CH$_2$OAr); 3.54 (4H, m, N(CH$_2$CH$_2$)$_2$O); 4.08 (2H, t, J=6 Hz, NCH$_2$CH$_2$OAr); 6.64 (2H, d, J=9 Hz, aromatic o to OH); 6.82 (1H, q, J$_{H4-H5}$=9 Hz, J$_{H5-H7}$=2 Hz, H5 of benzothiophene ring); 6.89 (2H, d, J=9 Hz, aromatic o to OCH$_2$); 7.15 (2H, d, J=9 Hz, aromatic m to OH); 7.23 (1H, d, J=9 Hz, H4 of benzothiophene ring); 7.31 (1H, d, J=2 Hz, H7 of benzothiophene ring); 7.63 (2H, d, J=9 Hz, aromatic o to CO); 9.68 (1H, s, OH); 9.72 (1H, s, OH). High resolution mass spectrum: calculated for C$_{27}$H$_{25}$NO$_5$S: 475.14533, found 475.14561.

EXAMPLE 24

6-hydroxy-2-(4-hydroxyphenyl)-3-[4-(2-piperidinoethoxy)benzoyl]benzo[b]thiophene A 4 g. portion of 6-methanesulfonyloxy-2-(4-methanesulfonyloxyphenyl)-3-[4-(2-piperidinoethoxy)-benzoyl]benzo[b]thiophene, hydrochloride, was combined with 100 ml. of denatured alcohol and 10 ml. of 5 N sodium hydroxide, and stirred under reflux for 1.5 hours under a nitrogen atmosphere. The reaction mixture was then evaporated to dryness under vacuum, and the residue was dissolved in 200 ml. of water and washed with 300 ml. of diethyl ether. The water layer was degassed under vacuum, and then nitrogen was bubbled through it to remove all traces of ether. The mixture was then acidified with 1 N hydrochloric acid, and then made basic with excess sodium bicarbonate. The precipitate was collected by filtration and washed with cold water to obtain 2.4 g. of crude product. It was purified on a 2×30 cm. column of silica gel, eluting first with 700 ml. of 5% methanol in chloroform, followed by 1 liter of 10% methanol in chloroform. The impurities came off first, and the product-containing fractions were combined and evaporated under vacuum to obtain 1.78 g. of yellow oil. The oil was dissolved in 6 ml. of acetone, seeded and chilled in a freezer to obtain 1.2 g. of purified product, m.p. 143°-147°. The identity of the product was confirmed as follows: nmr spectrum (100 mHz in dmso-d$_6$) δ1.20–1.65 (6H, m, N(CH$_2$CH$_2$)$_2$CH$_2$); 2.30–2.45 (4H, m, N(CH$_2$CH$_2$)$_2$CH$_2$); 2.60 (2H, t, J=6 Hz, OCH$_2$CH$_2$N); 4.06 (2H, t, J=6 Hz, OCH$_2$CH$_2$N); 6.68 (2H, d, J=9 Hz, aromatic o to OH); 6.85 (1H, q, J$_{H4-H5}$=9 Hz, J$_{H5-H7}$=2 Hz, H5 of benzothiophene ring); 6.90 (2H, d, J=9 Hz, aromatic o to OCH$_2$CH$_2$N); 7.18 (2H, d, J=9 Hz, aromatic m to OH); 7.25 (1H, d, J=9 Hz, H4 of benzothiophene ring); 7.66 (2H, d, J=9 Hz, aromatic o to CO); 9.72 (2H, broad s, OH). Ultraviolet spectrum in ethanol: λ$_{max}$ (ε): 290 nm. (34,000). Electron impact mass spectrum M+ at m/e 473.

EXAMPLE 25

6-hydroxy-2-(4-hydroxyphenyl)-3-[4-(2-piperidinoethoxy)benzoyl]benzo[b]thiophene A 3.6 g. portion of 6-methanesulfonyloxy-2-(4-methanesulfonyloxyphenyl)-3-[4-(2-piperidinoethoxy)-benzoyl]benzo[b]thiophene was dissolved in 100 ml. of tetrahydrofuran and 40 ml. of methanol, and 10 ml. of 5 N sodium hydroxide was added. The mixture was stirred for 16 hours at ambient temperature, and was then worked up by the procedure of Example 24 above to obtain 3.5 g. of a yellow solid. The impure product was purified by column chromatography on silica gel, eluting with a gradient solvent from 5% methanol in chloroform to 30% methanol in chloroform. The product-containing fractions were evaporated to obtain 1.85 g. of oily product, which was recrystallized from acetone to obtain 1.25 g. of purified product, m.p. 141°-144°.

EXAMPLE 26

6-hydroxy-2-(4-hydroxyphenyl)-3-[4-(2-piperidinoethoxy)benzoyl]benzo[b]thiophene The oily product of Example 9 above, 6-acetoxy-2-(4-acetoxyphenyl)-3-[4-(2-piperidinoethoxy)benzoyl]benzo[b]thiophene, hydrochloride, was dissolved in 700 ml. of methanol and 100 ml. of 5 N sodium hydroxide. The mixture was stirred at ambient temperature for two hours, and was then evaporated to an oil under vacuum at a temperature below 40°. The residue was dissolved in 500 ml. of water and washed twice with 500 ml. portions of diethyl ether. The aqueous layer was acidified to pH 2 with cold 50% aqueous methanesulfonic acid, diluted to about 3 liters, and washed twice with 1 liter portions of diethyl ether. The aqueous layer was then separated, thoroughly degassed under vacuum, and made basic with aqueous ammonia. The resulting solids were collected by filtration and vacuum dried at 40° to obtain 14.2 g. of crude product which was chromatographed over a 5×5 cm. column of Activity I silica gel, eluting with 15% methanol in chloroform. The product-containing fractions were evaporated to dryness to obtain a yellow foam, which was recrystallized from acetone to obtain 11.9 g. of product, which was substantially identical to the product of Example 24 above by nmr, ultraviolet and infrared analysis.

EXAMPLE 27

6-hydroxy-2-(4-hydroxyphenyl)-3-[4-(2-piperidinoethoxy)benzoyl]benzo[b]thiophene The crude product of Example 10 above, 6-benzoyloxy-2-(4-benzoyloxyphenyl)-3-[4-(2-piperidinoethoxy)benzoyl]benzo[b]thiophene, hydrochloride, was combined with 400 ml. of ethanol, 400 ml. of water and 55 ml. of methanesulfonic acid. The mixture was stirred on the steam bath for 72 hours, and was then evaporated down to an oil which was diluted to about 6 liters with water. The aqueous solution was washed twice with 1 liter portions of diethyl ether, and was then thoroughly degassed under vacuum, cooled to about 20°, and made basic with aqueous ammonia to pH 8.4. The product which precipitated was collected by filtration and vacuum dried, and was then recrystallized from about 80 ml. of acetone. The product was vacuum dried at 40° to obtain 18.1 g. of crystals which was found by nmr, mass spectrum, infrared and ultraviolet analysis to be substantially identical to the product of Example 24.

EXAMPLE 28

6-hydroxy-2-(4-hydroxyphenyl)-3-[4-(2-piperidinoethoxy)benzoyl]benzo[b]thiophene The oily 6-benzenesulfonyloxy-2-(4-benzenesulfonyloxyphenyl)-3-[4-(2-piperidinoethoxy)benzoyl]benzo[b]thiophene, hydrochloride, which was prepared in Example 11 above was added to 300 ml. of denatured ethanol and 30 ml. of 5 N sodium hydroxide under a nitrogen atmosphere, and stirred under reflux for two hours. The mixture was then evaporated under vacuum, and the residue was dissolved in 600 ml. of water, which was washed with 800 ml. of diethyl ether. The aqueous layer was made acid to pH 2.0 with methanesulfonic acid, diluted to 6 liters with additional water, and washed twice with 2-liter portions of diethyl ether. The aqueous layer was degassed under vacuum, and made basic to pH 8.4 with aqueous ammonia. The resulting yellow-brown crystals were collected, washed with water and vacuum dried at 40° to obtain 7.4 g. of the expected product. A final recrystallization of the product from acetone provided light tan crystals which by nmr, infrared, and ultraviolet spectra were substantially identical to the desired product prepared in Example 24 above.

The next group of examples illustrates the variation of the process of this invention wherein the protected dihydroxy starting compound is acylated with an acylating agent bearing a leaving group, X, which leaving group is then displaced with an amine to provide the basic side chain.

EXAMPLE 29

6-methanesulfonyloxy-2-(4-methanesulfonyloxyphenyl)-3-(4-[2-chloroethoxy)benzoyl]benzo[b]thiophene The acid chloride was prepared from 1.1 g. of 4-(2-chloroethoxy)benzoic acid as described in Example 9, and the acid chloride was combined with 1.2 g. of 6-methanesulfonyloxy-2-(4-methanesulfonyloxyphenyl)-benzo[b]thiophene in 25 ml. of 1,2-dichloroethane in the presence of 0.5 ml. of trifluoromethanesulfonic acid. The mixture was stirred under reflux for 2 hours and was then poured into ice-water. The organic layer was separated, extracted with sodium bicarbonate solution, dried over magnesium sulfate and concentrated under vacuum to obtain 1.9 g. of impure product. Chromatography over a 4×8 cm. silica gel column, eluting with 9/1 toluene/ethyl acetate gave 1.2 g. of impure intermediate product, which was recrystallized from methanol to provide white crystals, m.p. 123°-124°. The absorption maximum for the CO function appeared at 1650 cm.$^{-1}$ in the infrared spectrum taken in chloroform.

EXAMPLE 30

6-methanesulfonyloxy-2-(4-methanesulfonyloxyphenyl)-3-[4-(2-bromoethoxy)benzoyl]benzo[b]thiophene One g. of 4-(2-bromoethoxy)benzoic acid was converted to the acid chloride, and was combined with 1.2 g. of 6-methanesulfonyloxy-2-(4-methanesulfonyloxyphenyl)benzo[b]thiophene, 20 ml. of dichloromethane and 0.5 ml. of trifluoromethanesulfonic acid. The mixture was stirred under reflux overnight, and was then poured into ice-water. The organic layer was separated, washed with sodium carbonate solution, dried and evaporated under vacuum to obtain 2.1 g. of brown oil.

The oil was chromatographed over a 4×8 cm. silica gel column with 9/1 toluene/ethyl acetate and the product-containing fractions were combined and evaporated under vacuum to obtain 1.8 g. of purified product as an oil. The product was identified by its MH+ molecular ion, m/e 626, in the field desorption mass spectrum and by an absorption maximum in the infrared spectrum, in chloroform, at 1645 cm.$^{-1}$ attributable to the CO function. A small sample was recrystallized from methanol to obtain white crystals, m.p. 105°-107°.

EXAMPLE 31

6-methanesulfonyloxy-2-(4-methanesulfonyloxyphenyl)-3-[4-(2-piperidinoethoxy)benzoyl]benzo[b]thiophene, hydrochloride A 1.5 g. portion of 6-methanesulfonyloxy-2-(4-methanesulfonyloxyphenyl)-3-[4-(2-bromoethoxy)benzoyl]benzo[b]thiophene was combined with 5 ml. of piperidine, 25 ml. of anhydrous dimethylformamide and 150 mg. of potassium iodide. The mixture was stirred at ambient temperature for two hours, and was then evaporated to dryness under vacuum. To the residue was added 25 ml. of saturated aqueous sodium bicarbonate and the mixture was extracted with two 25 ml. portions of ethyl acetate. The organic layers were combined and washed five times with 20 ml. portions of aqueous sodium chloride, dried over magnesium sulfate and evaporated under dryness to a brown oil. To the oil was added 50 ml. of 3% hydrogen chloride in methanol, and the mixture was evaporated to dryness again. To it was added 10 ml. of methanol, and the mixture was warmed and evaporated down to about 8 ml. It was then cooled, and the purified intermediate product, m.p. 128°-130°, precipitated. About 1.6 g. of purified intermediate product was obtained.

EXAMPLE 32

6-methanesulfonyloxy-2-(4-methanesulfonyloxyphenyl)-3-[4-(2-piperidinoethoxy)benzoyl]benzo[b]thiophene, hydrochloride An 0.58 g. portion of 6-methanesulfonyloxy-2-(4-methanesulfonyloxyphenyl)-3-[4-(2-chloroethoxy)benzoyl]benzo[b]thiophene was combined with 20 ml. of dimethylformamide, 4.8 ml. of piperidine and 100 mg. of potassium iodide, and the mixture was stirred overnight at 40° and then at 50° for two hours. The mixture was evaporated to a brown oil under vacuum, and the oil was worked up by pouring it into 50 ml. of saturated aqueous sodium bicarbonate and extracting the mixture twice with 40 ml. portions of ethyl acetate. The organic layers were combined, washed twice with 100 ml. portions of saturated aqueous sodium chloride and concentrated under vacuum to an oil. To the oily residue was added 50 ml. of 3% hydrogen chloride in methanol, and the acidic mixture was concentrated again to an oil, which was dissolved in hot denatured ethanol and crystallized. The first crop of purified crystals amounted to 0.4 g. and had a melting point and infrared and ultraviolet spectra identical to those of the products of Examples 12 and 31.

EXAMPLE 33

6-methanesulfonyloxy-2-(4-methanesulfonyloxyphenyl)-3-[4-(2-pyrrolidinoethoxy)benzoyl]benzo[b]thiophene, hydrochloride A 1.19 g. portion of the product of Example 30 above, 20 ml. of anhydrous dimethylformamide and 3.4 g. of freshly distilled pyrrolidine were added to a flask at 25°, and then 100 mg. of powdered potassium iodide was added and the mixture was stirred at ambient temperature for 1 hour. The mixture was then evaporated under vacuum, 25 ml. of saturated aqueous sodium bicarbonate was added, and the mixture was extracted twice with 25 ml. portions of ethyl acetate. The extract was washed five times with 20 ml. portions of aqueous sodium chloride, and was dried over magnesium sulfate and evaporated to a brown oil. The oil was dissolved in 25 ml. of hydrochloric acid in methanol, which had been prepared by addition of 10 ml. of acetyl chloride to 100 ml. of methanol under nitrogen at 0°. The mixture was then evaporated to dryness under vacuum, and the resulting foam was crystallized from denatured ethanol to provide 1.07 g. of crystals, m.p. 206°-207°.

The compounds are useful for estrogenic, antiestrogenic and antiandrogenic therapy. Accordingly, they are useful in treating pathological conditions of endocrine target organs, which conditions are dependent or partially dependent on an estrogen or on an androgen. Such conditions include mammary cancer, mammary fibrocystic disease, cancer of the prostate, and benign prostatic hypertrophy.

U.S. Pat. No. 4,133,814 teaches that certain of the compounds are also useful as anti-cancer and anti-fertility drugs. The antiestrogenic and antiandrogenic efficacy of a preferred compound prepared by this invention, 6-hydroxy-2-(4-hydroxyphenyl)-3-[4-(2-piperidinoethoxy)benzoyl]benzo[b]thiophene, is explained in further detail in the application of Charles D. Jones entitled Antiestrogenic and Antiandrogenic Benzothiophene, which was filed on the same day as was this application.

The dose of a compound to be administered to a human is rather widely variable. It should be noted that it may be necessary to adjust the dose of a compound when it is administered in the form of a salt, such as a laurate, the salt-forming moiety of which has an appreciable molecular weight. The general range of effective administration rates of the compounds is from about 0.05 mg/kg./day to about 50 mg./kg./day. A preferred rate range is from about 0.1 mg./kg./day to about 10 mg./kg./day, and the most highly preferred range is from about 0.1 mg./kg./day to about 5 mg./kg./day. Of course, it is often practical to administer the daily dose of a compound in portions, at various hours of the day.

The route of administration of the compounds is not critical. The compounds are known to be absorbed from the alimentary tract, and so it is usually preferred to administer a compound orally for reasons of convenience. However, the compounds may equally effectively be administered percutaneously, or as suppositories for absorption by the rectum, if desired in a given instance.

The compounds are usually administered as pharmaceutical compositions. All of the usual types of compositions may be used including tablets, chewable tablets, capsules, solutions, parenteral solutions, troches, suppositories and suspensions. Compositions are formulated to contain a daily dose, or a convenient fraction of a daily dose, in a dosage unit, which may be a single tablet or capsule or a convenient volume of a liquid. In general, compositions contain from about 0.000006% to about 60% of compound, depending on the desired dose and the type of composition to be used.

The activity of the compounds does not depend on the composition in which it is administered or on the concentration of the composition. Thus, the compositions are chosen and formulated solely for convenience and economy.

We claim:

1. A process for preparing a compound of the formula

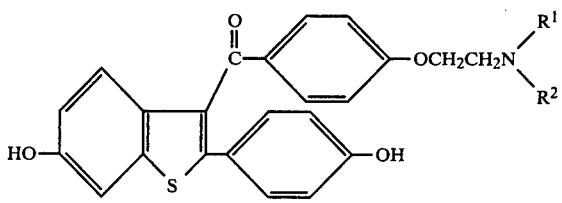

wherein $R^1$ and $R^2$ are independently $C_1$–$C_4$ alkyl, or combine to form $C_4$–$C_6$ polymethylene or —$(CH_2)_2O(CH_2)_2$—; which process comprises acylating a compound of the formula

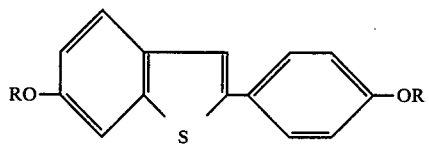

wherein R is —$COR^3$ or —$SO_2CH_3$, and $R^3$ is methyl, phenyl, p-tolyl, p-anisyl, or mono- or di(halo or nitro)-phenyl; under Friedel-Crafts conditions with an acylating agent of the formula

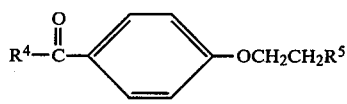

wherein $R^5$ is X or

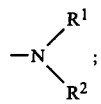

X is chloro, bromo or —$SO_2R^3$; and $R^4$ is chloro, bromo, iodo, or an activating ester group; when $R^5$ is X, displacing the X group with an amine of the formula

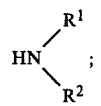

and cleaving the R groups.

2. A process of claim 1 wherein the starting compound is a compound wherein R is —$COR^3$.

3. A process of claim 2 wherein the starting compound is a compound wherein $R^3$ is methyl.

4. A process of claim 2 wherein the starting compound is a compound wherein $R^3$ is phenyl.

5. A process of claim 2 wherein the starting compound is a compound wherein $R^3$ is p-anisyl.

6. A process of claim 1 wherein the starting compound is a compound wherein R is —$SO_2CH_3$.

7. A process of any one of claims 1-6 wherein the acylating agent is a compound wherein $R^5$ is pyrrolidino or piperidino.

8. A process of claim 7 wherein the acylation is in the presence of aluminum chloride.

9. A process of claim 7 wherein the acylation is in the presence of trifluoromethanesulfonic acid.

10. A process of claim 8 wherein the acylating agent is a compound wherein $R^4$ is chloro or bromo.

11. A process of claim 9 wherein the acylating agent is a compound wherein $R^4$ is chloro or bromo.

12. A process of any one of claims 1-6 wherein the acylating agent is a compound wherein $R^5$ is X.

13. A process of claim 12 wherein the acylating agent is a compound wherein X is chloro or bromo.

14. A process of claim 13 wherein the acylation is in the presence of aluminum chloride.

15. A process of claim 14 wherein the acylating agent is a compound wherein $R^4$ is chloro or bromo.

16. A process of claim 13 wherein the acylation is in the presence of trifluoromethanesulfonic acid.

17. A process of claim 16 wherein the acylating agent is a compound wherein $R^4$ is chloro or bromo.

18. A process of claim 12 wherein the group X is displaced with piperidine or pyrrolidine.

19. A process of claim 13 wherein the group X is displaced with pyrrolidine or piperidine.

\* \* \* \* \*

UNITED STATES PATENT AND TRADEMARK OFFICE
CERTIFICATE OF CORRECTION

PATENT NO. : 4,358,593
DATED : November 9, 1982
INVENTOR(S) : Charles D. Jones and Mary E. Goettel It is certified that error appears in the above-identified patent and that said Letters Patent are hereby corrected as shown below:

Column 13, line 18, "NH($CH_2\underline{CH}_2$)$_2\underline{CH}_2$ and $OCH_2CH_2N$)" should read --NH($\underline{CH}_2CH_2$)$_2CH_2$ and $OCH_2\underline{CH}_2N$)--.

Column 13, line 19, "$OCH_2\underline{CH}_2N$)" should read --$OC\underline{H}_2CH_2N$)--.

Column 14, line 11, "$OCH_2CH_2N$)" should read --$OC\underline{H}_2CH_2N$)--.

Column 14, line 12, "$OC\underline{H}_2$)" should read --$OCH_2$)--.

Column 15, line 30, "N($CH_2\underline{CH}_2$)$_2$" should read --N($\underline{CH}_2CH_2$)$_2$--.

Column 15, line 31, "$OCH_2CH_2N$)" should read --$OCH_2\underline{CH}_2N$)--.

Column 18, line 68, "$cm^{31\ 1}$" should read --$cm^{-1}$--.

Signed and Sealed this

Eighth Day of March 1983

[SEAL]

Attest:

GERALD J. MOSSINGHOFF

Attesting Officer    Commissioner of Patents and Trademarks